(12) United States Patent
Lööf et al.

(10) Patent No.: US 10,881,804 B2
(45) Date of Patent: Jan. 5, 2021

(54) MEDICAMENT DELIVERY DEVICE

(71) Applicant: CAREBAY EUROPE LTD, Sliema (MT)

(72) Inventors: Stefan Lööf, Sköndal (SE); Stefan Morén, Kista (SE)

(73) Assignee: SHL MEDICAL AG, Zug (CH)

( * ) Notice: Subject to any disclaimer, the term of this patent is extended or adjusted under 35 U.S.C. 154(b) by 354 days.

(21) Appl. No.: 16/047,309

(22) Filed: Jul. 27, 2018

(65) Prior Publication Data

US 2018/0344937 A1 Dec. 6, 2018

Related U.S. Application Data

(63) Continuation of application No. 14/915,239, filed as application No. PCT/EP2014/067871 on Aug. 21, 2014, now Pat. No. 10,149,942.

(30) Foreign Application Priority Data

Aug. 29, 2013 (SE) ...................................... 1350995

(51) Int. Cl.
*A61M 5/315* (2006.01)
*A61M 5/20* (2006.01)
(Continued)

(52) U.S. Cl.
CPC ...... *A61M 5/31501* (2013.01); *A61M 5/2033* (2013.01); *A61M 5/28* (2013.01);
(Continued)

(58) Field of Classification Search
CPC .......... A61M 5/31501; A61M 5/31571; A61M 5/2033; A61M 2005/2073
See application file for complete search history.

(56) References Cited

U.S. PATENT DOCUMENTS

2003/0105430 A1* 6/2003 Lavi .................... A61M 5/2033
604/136
2005/0101919 A1 5/2005 Brunnberg
(Continued)

FOREIGN PATENT DOCUMENTS

WO 94/13342 A1 6/1994
WO 2010/000559 A1 1/2010
(Continued)

OTHER PUBLICATIONS

EPO, Int'l Search Report in PCT/EP2014/067781, dated Feb. 12, 2015.
EPO, Written Opinion in PCT/EP2014/067781, dated Feb. 12, 2015.

*Primary Examiner* — Jason E Flick
*Assistant Examiner* — Tasnim Mehjabin Ahmed
(74) *Attorney, Agent, or Firm* — McDonnell Boehnen Hulbert & Berghoff LLP

(57) ABSTRACT

The present invention relates to a medicament delivery device comprising a housing, which housing is arranged to accommodate a medicament container, a drive unit operably arranged to act on said medicament container for expelling a dose of medicament, the drive unit comprising a plunger rod, a force element operably connected to said plunger rod, a connector arranged to releasibly hold said plunger rod, an actuator element operably arranged to said connector and a manually operable actuator arranged to act on said actuator element for releasing said connector when operated. The invention is characterised in a safety device arranged to releasibly hold said actuator element in a locking position with said connector, preventing unintended release of said plunger rod.

20 Claims, 11 Drawing Sheets

(51) Int. Cl.
*A61M 5/28* (2006.01)
*A61M 5/24* (2006.01)

(52) U.S. Cl.
CPC .... *A61M 5/31515* (2013.01); *A61M 5/31571* (2013.01); *A61M 5/2066* (2013.01); *A61M 5/2448* (2013.01); *A61M 2005/2073* (2013.01)

(56) References Cited

U.S. PATENT DOCUMENTS

| | | | |
|---|---|---|---|
| 2009/0240195 A1 | 9/2009 | Schrul et al. | |
| 2010/0049125 A1* | 2/2010 | James | A61M 5/2033 |
| | | | 604/110 |
| 2011/0306936 A1 | 12/2011 | Holmqvist | |
| 2013/0218086 A1 | 8/2013 | Wotton et al. | |

FOREIGN PATENT DOCUMENTS

| | | |
|---|---|---|
| WO | 2010//066591 A1 | 6/2010 |
| WO | 2012/105898 A1 | 8/2012 |

* cited by examiner

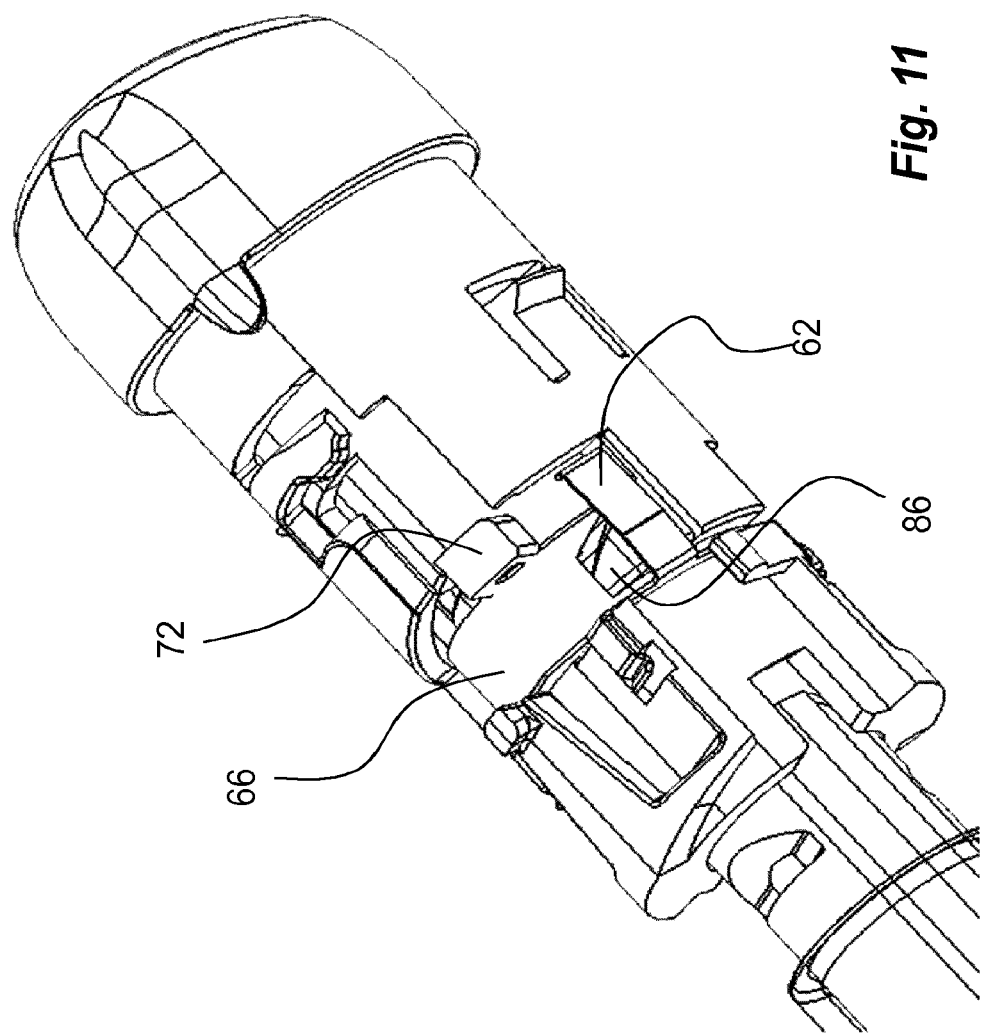

MEDICAMENT DELIVERY DEVICE

CROSS REFERENCE TO RELATED APPLICATIONS

The present application is a continuation of U.S. patent application Ser. No. 14/915,239, filed Feb. 28, 2016, which is a U.S. National Phase Application pursuant to 35 U.S.C. § 371 of International Application No. PCT/EP2014/067871 filed Aug. 21, 2014, which claims priority to Swedish Patent Application No. 1350995-5 filed Aug. 29, 2013. The entire disclosure contents of these applications are herewith incorporated by reference into the present application.

TECHNICAL FIELD

The present invention relates to a medicament delivery device and in particular to a device arranged with features and functions actuated by a user manually operating the device, wherein the device is arranged with enhanced safety features preventing unintentional activation.

BACKGROUND

Many medicament delivery devices on the market today are arranged with a number of features that facilitate the use of the device because today's devices are more and more intended to be handled by the patients themselves. The added functionality may be an advantage when the medicament delivery devices comprise injection needles since many patients feel uncomfortable seeing the needle and also feel reluctant regarding penetration of the needle. In that respect, added functionality may include features such as automatic penetration mechanisms as well as automatic injection mechanisms.

Many medicament delivery devices that are arranged with automatic features and functions are often also arranged with some sort of actuation member that is operated by a user either indirectly when pressing the device against a dose delivery site or directly by operating an activation button on the device, such as at the distal end thereof.

Document WO 2012/105898 discloses an activating mechanism comprising an actuator in the form of a button protruding through the distal end of the housing part. The actuator is arranged to act on an actuator member comprised in a power unit of the device. The actuator member is arranged as a ring-shaped element that can be moved axially by the actuator. In one position, the actuator member locks movement of holding elements that are arranged to interact and hold a plunger rod in a tensioned state by a force member. The actuator may then move the actuator member to a release position where the holding elements may be moved out of engagement with the plunger rod, whereby the latter is free to move in the proximal direction by the force member, thereby enabling delivery of a dose of medicament.

The function of the power unit of WO 2012/105898 has proven to work in most instances. However, in some cases when the device has been accidentally dropped on a hard surface such as a table, a floor or the ground, impact forces may cause the actuator member to move from the locking position to the release position, thereby activating the device such that a dose is delivered unintentionally.

The dose is then wasted. If the device is a single-use device, then the device has to be discarded without having delivered any medicament to the patient and a new device has to be obtained. Even if the device is re-usable, it has to be reloaded in order to deliver a new dose. Both obtaining a new device or reloading a device is time-consuming and causes stress to a patient, especially in urgent situations.

There is thus a demand for devices having an increased functionality for minimizing the risk of activation after accidental drops and other types of accidental impacts.

SUMMARY

As used herein, the term "liquid" encompasses all fluids, solutions, suspensions, emulsions, oils, gels and so forth, which generally behave as liquids at operating temperatures. The term explicitly includes solid compositions dissolved or dispersed in a liquid carrier. Materials behaving as highly viscous liquids are also included.

In the present application, when the term "distal part/end" is used, this refers to the part/end of the device, or the parts/ends of the members thereof, which under use of the device is located the furthest away from the medicament delivery site of the patient. Correspondingly, when the term "proximal part/end" is used, this refers to the part/end of the device, or the parts/ends of the members thereof, which under use of the device is located closest to the medicament delivery site of the patient.

The aim of the present invention is to remedy the drawbacks of the state of the art medicament delivery devices. This aim is obtained with a medicament delivery device according to the features of the independent patent claim. Preferable embodiments of the invention form the subject of the dependent patent claims.

According to an aspect, it comprises a medicament delivery device comprising a housing. The housing may be in one or several parts wherein the latter case the housing parts may be fixedly attached to each other or movably attached in relation to each other, depending on the application and also type of medicament to be used. The housing, or some of the housing parts, may preferably be arranged to accommodate a medicament container. The medicament container may be of several possible designs, such as syringes, cartridges, ampoules or the like. The medicament container may further be arranged with one or several compartments containing medicament. In the latter case, the compartments may contain medicament components and diluents that are to be mixed before delivery.

Preferably a drive unit may be operably arranged to act on said medicament container for expelling a dose of medicament. The drive unit may comprise a plunger rod arranged to act on a stopper or the like inside the medicament container. In case of multi-chamber containers, several stoppers may be moved by the plunger rod, both in order to mix the components and also for delivering a dose of medicament.

A resilient force member may advantageously be operably connected to said plunger rod for driving the plunger rod when delivering a dose of medicament. The force member may have a number of designs within the scope of the invention, such as compression springs, torsion springs, leaf springs, clock springs, gas springs, just to mention some examples.

The drive unit may further comprise a connection member arranged to releasibly hold said plunger rod when preferably the force member is in a tensioned state. Further, an actuator member may be operably arranged to said connection member as well as a manually operable actuator arranged to act on said actuator member for releasing said connection member when operated. With this solution, the actuator may be operated by a user with his/her hand or fingers, which in turn causes the actuator member to act on the connection member such that the plunger rod is released. Due to the force of the force member, the plunger rod will then act on the stoppers of the medicament container such that a dose of medicament is delivered to the user via a suitable medicament delivery member. The latter may e.g. be an injection needle, a nozzle, a mouth or nasal piece a nebulizer etc.

According to a favourable solution, it is characterised in a safety device arranged to releasibly hold said actuator member in a locking position with said connection member, preventing unintended release of said plunger rod. With this solution it is ascertained that the actuator member is immovable prior to the manual operation of the actuator by a user. This is a clear advantage and enhanced safety aspect if for example the medicament delivery device should be accidentally dropped on a hard surface such as a table or a floor. Without the safety device, there is a risk that the actuator member may be displaced by impact forces, which in turn could cause the device to be unintentionally triggered and a dose to be wasted. This situation may be critical if the user has only one medicament delivery device at hand and the delivery of a dose of medicament at that time is important or vital. With the safety device according to the preferred solution, the risk is minimized or greatly reduced.

According to one another aspect, the connection member may comprise generally radially movable connection elements capable of releasibly holding said plunger rod and wherein said actuator member is arranged axially movable from a locking position to a release position of said connection elements. The actuator member will then in the locking position prevent the connection elements from moving in the radial direction, thus ensuring a firm hold of the plunger rod. When moved axially to the release position, the connection elements will be free to move in the radial direction, thereby causing a release of the tensioned plunger rod.

Preferably the safety device comprises elements arranged to prevent movement of said actuator member from said locking position to said release position until activated. In one solution, the safety elements may be designed as a number of flexible arms protruding distally in a generally longitudinal direction towards said actuator member. This provides a positive blocking action against unintentional movement of the actuator member.

The safety device may be made of a number of materials having the desired properties. However according to one favourable solution, at least parts of said safety device are made of metal. The use of metal has the advantage that it has a high strength to dimension ratio. Thus, the safety elements may for example be made with reduced thickness in comparison to comparable plastic designs. This further has the advantage that the safety elements occupy less space inside the medicament delivery device, thus not affecting the overall size of the device. It is however to be understood that the solution is not limited to metal, other types of material and combinations of materials may be used depending on application and design criteria.

Preferably the medicament delivery device may further comprise an activation member operably arranged to, upon manual operation, activate said safety device to allow movement of said actuator member. Thus, in order to make the device ready for delivery of a dose of medicament, the activation member is operated such that the safety device is activated to allow subsequent dose delivery.

According to a further aspect, said activation member may comprise elements capable of moving said safety elements out of contact with said actuator member. In this respect the solution may comprise protrusions capable of moving said flexible arms outwardly in a radial direction when said activation member is operated.

These and other aspects of, and advantages with, the present invention will become apparent from the following detailed description of the invention and from the accompanying drawings.

BRIEF DESCRIPTION OF THE FIGURES

In the following detailed description of the invention, reference will be made to the accompanying drawings, of which FIG. 11 is a perspective view of a third functional state of the device of FIG. 1.

DETAILED DESCRIPTION

Figure 1:
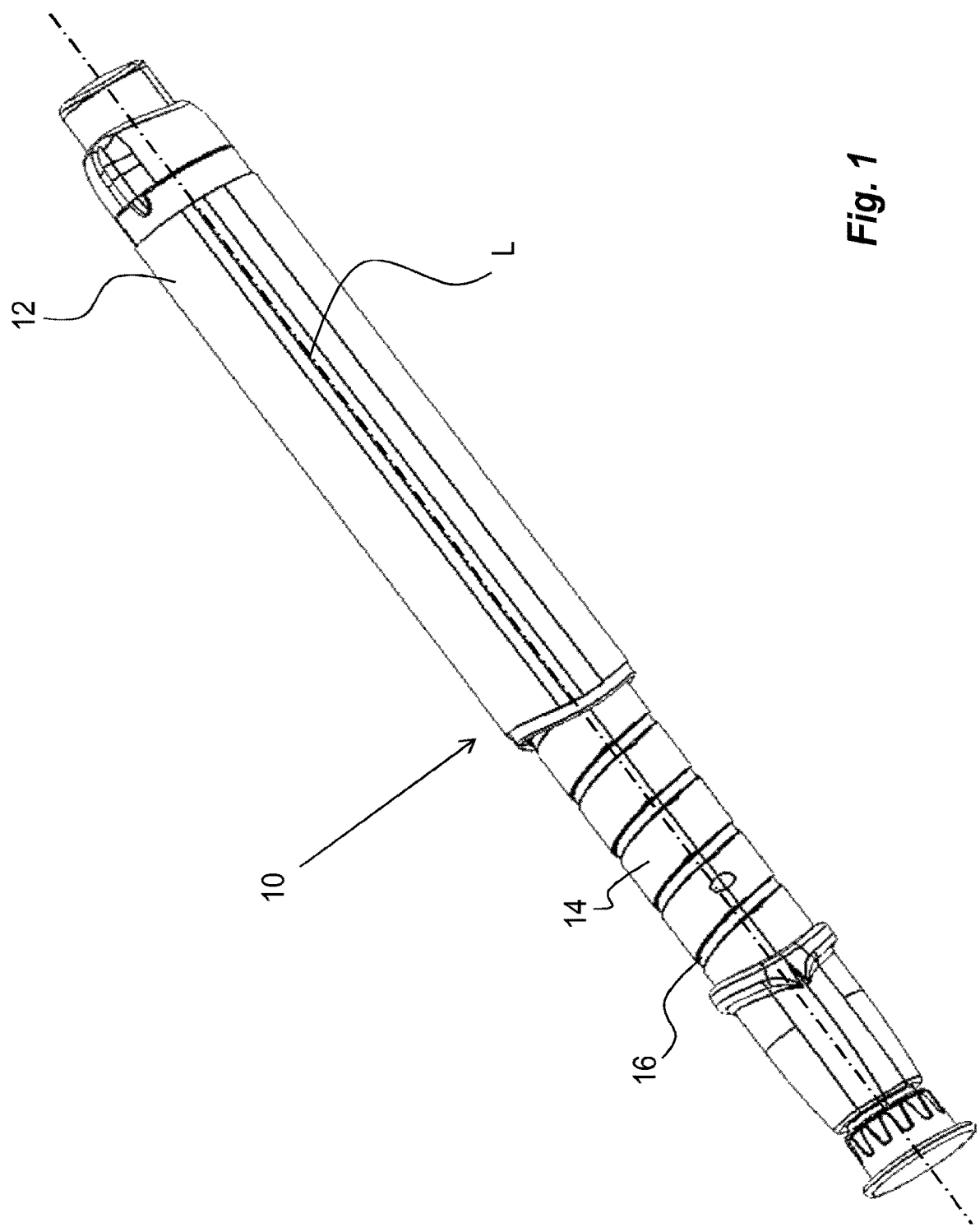
FIG. 1 is a perspective view of one embodiment of a medicament delivery device.

The exemplary embodiment of a medicament delivery device 10 is shown in the drawings. It comprises a distal housing part 12 and a proximal housing part 14. The two housing parts are in the embodiment shown intended and arranged to be interconnected with connection elements. As an example, the connection elements may comprise threads 16, FIG. 1, on an outer surface of the proximal housing part arranged to cooperate with corresponding threads or thread segments (not shown) on an inner surface of the distal housing part 12. In this respect it is to be understood that many other types of connection elements may be utilized for attaching the housing parts, such as e.g. bayonet connections or snap-in elements.

Figure 2:
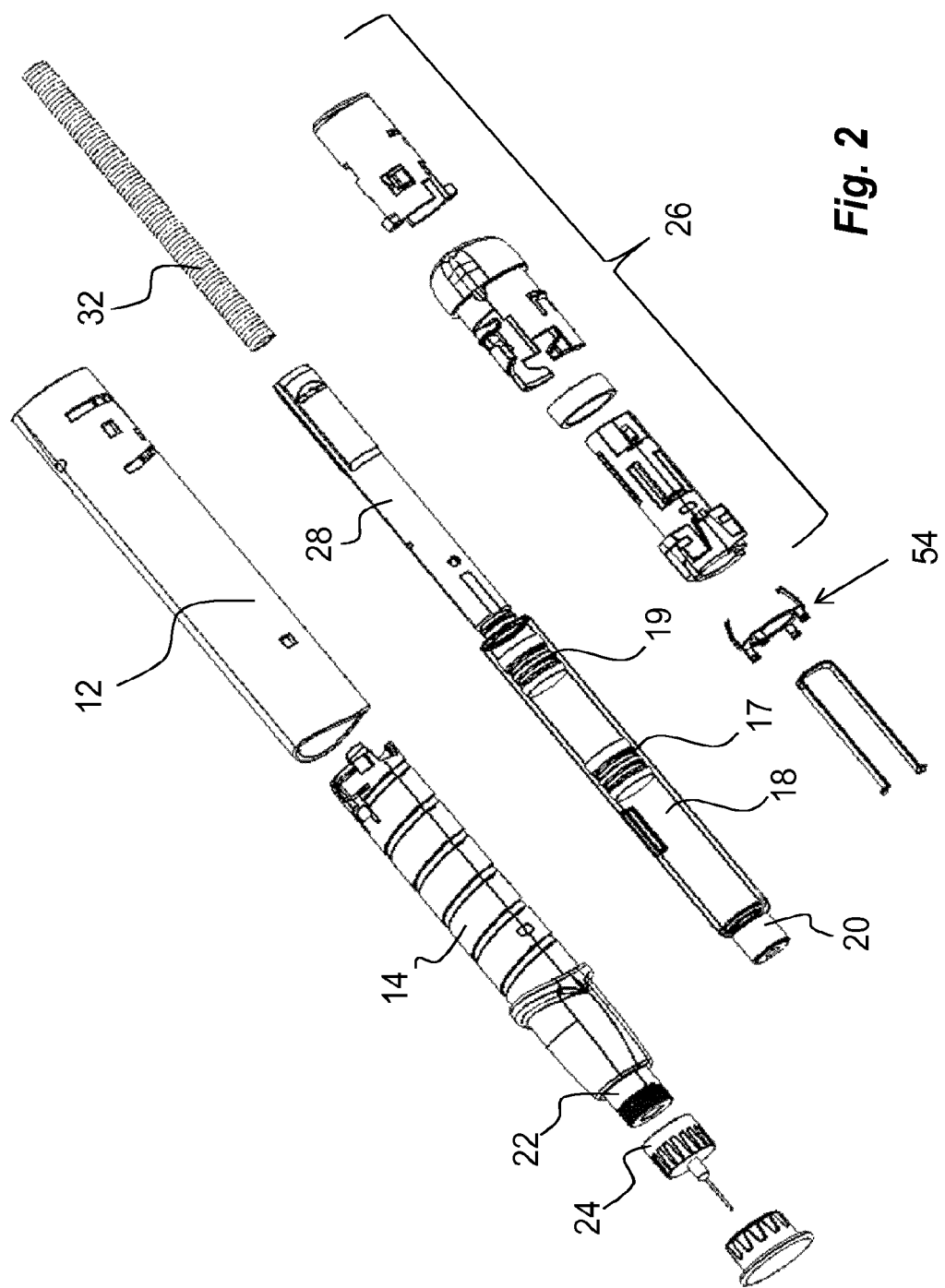
FIG. 2 is an exploded view of the embodiment of FIG. 1.

The embodiment shown is designed for handling a multi-chamber medicament container 18, FIG. 2, and thus the proximal housing part 14 is arranged to accommodate a medicament container, in the embodiment shown a dual chamber container where one chamber contains the medicament in powder form and the other chamber contains a diluent. The two chambers are divided by a movable first stopper 17. At the distal end of the medicament container a second movable stopper 19 is arranged. The medicament container is further arranged with a proximally directed neck portion, 20 which is intended to fit into a proximally directed neck portion 22 of the proximal housing part 14, FIG. 2. Further, the outer surface of the neck portion 22 of the proximal housing part 14 is arranged with connection elements for connecting a medicament delivery member 24. The connection elements may be threads, a bayonet connection, luer-lock connections, snap-on connections etc. Further the medicament delivery member may be an injection needle, a mouth or nasal piece, a nebulizer nozzle, etc.

Figure 3:
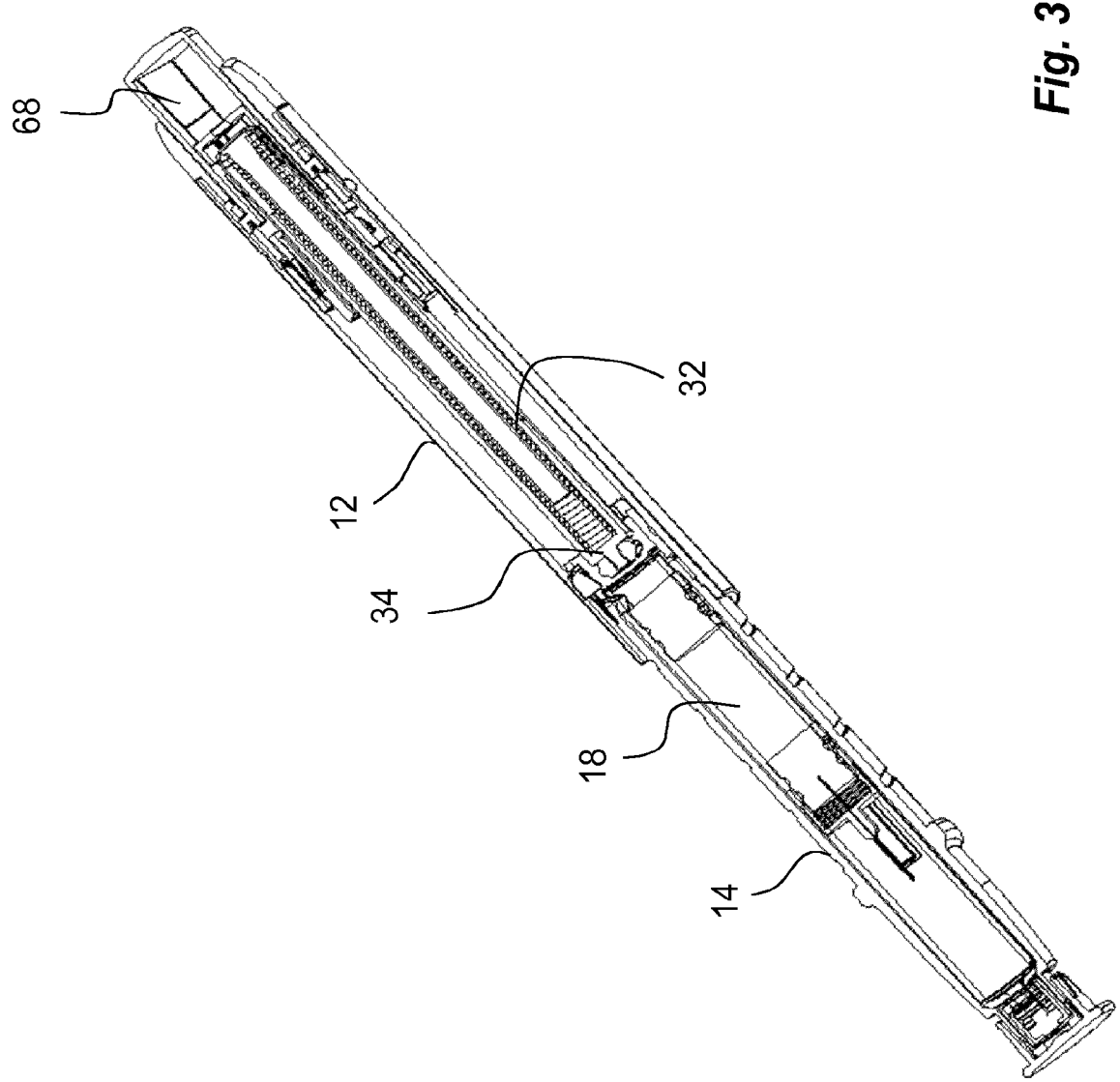
FIG. 3 is cross-sectional longitudinal view of the embodiment of FIG. 1.
Figure 4:
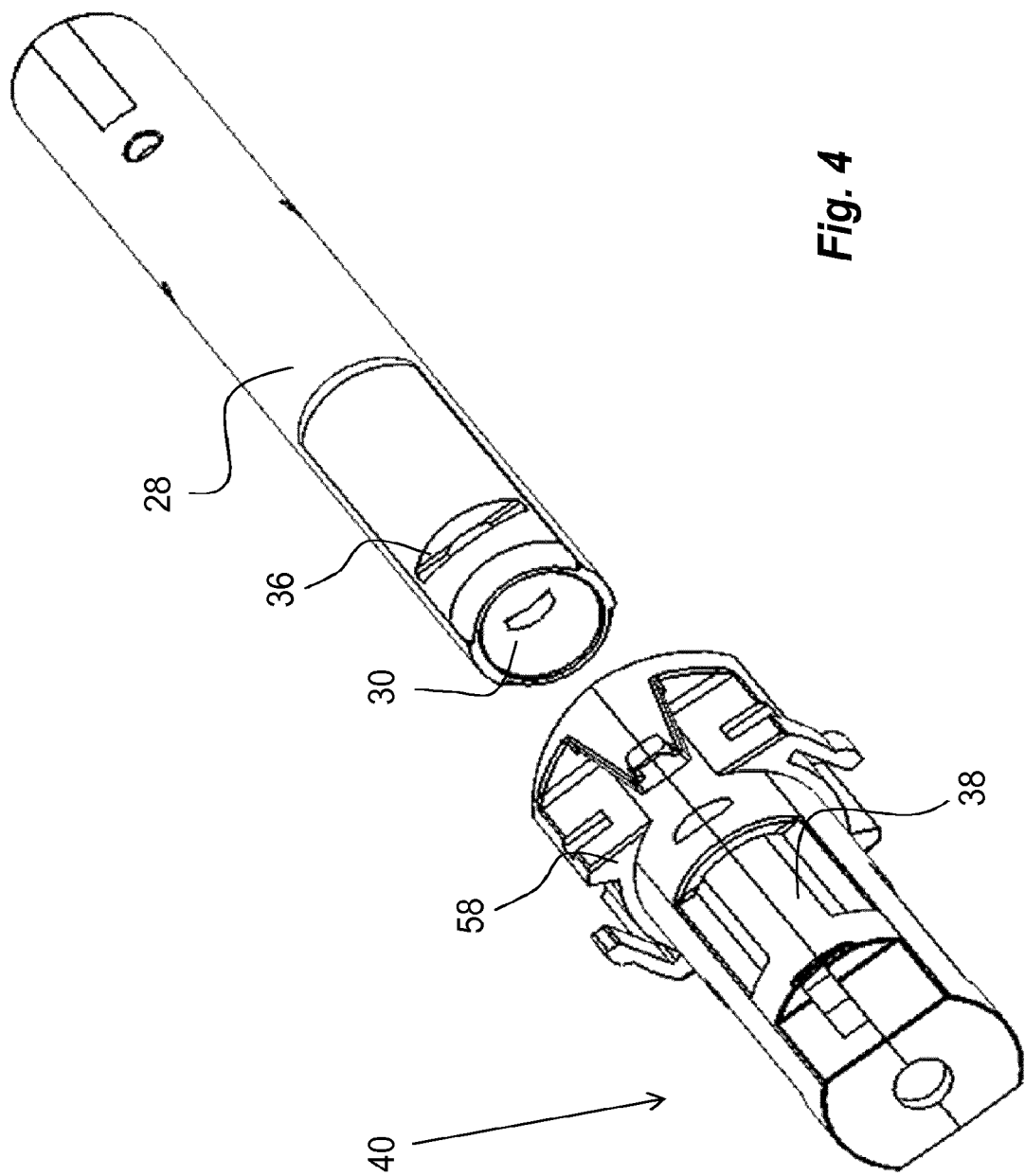
FIG. 4 is a perspective view of the connector and plunger rod of the embodiment of FIG. 1.

The embodiment according to the figures further comprises a drive unit 26, FIG. 2. The drive unit comprises a generally elongated tubular plunger rod 28, FIGS. 2 and 4, provided with a longitudinal cavity 30, FIG. 4, in which a resilient force element 32 is placed. In the embodiment shown the force element 32 is a compression spring, where its proximal end is in contact with an end wall 34 of the cavity 30, FIG. 3. The distal area of the plunger rod 28 is arranged with two recesses 36 on opposite sides of the plunger rod, FIG. 4. These recesses 36 are arranged to cooperate with holding elements 38 on a connector 40 comprised in the drive unit 26. The holding elements 38 are in the embodiment shown arranged as radially flexible tongues arranged with inwardly protruding hooks 42, FIG. 5, which hooks fit into the recesses 36 of the plunger rod 28.

Figure 5:
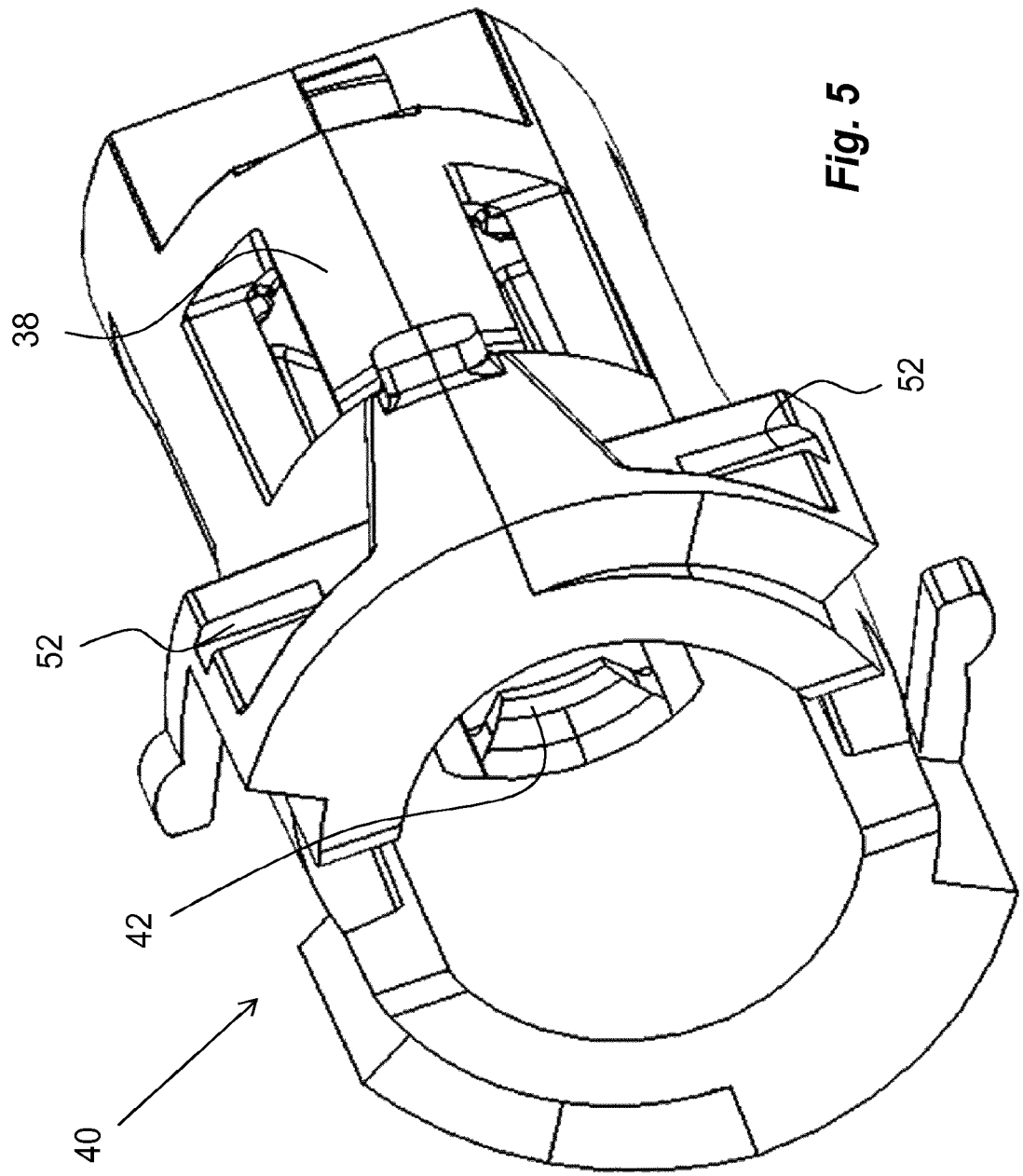
FIG. 5 is a perspective view of the connector of the embodiment of FIG. 1.
Figure 6:
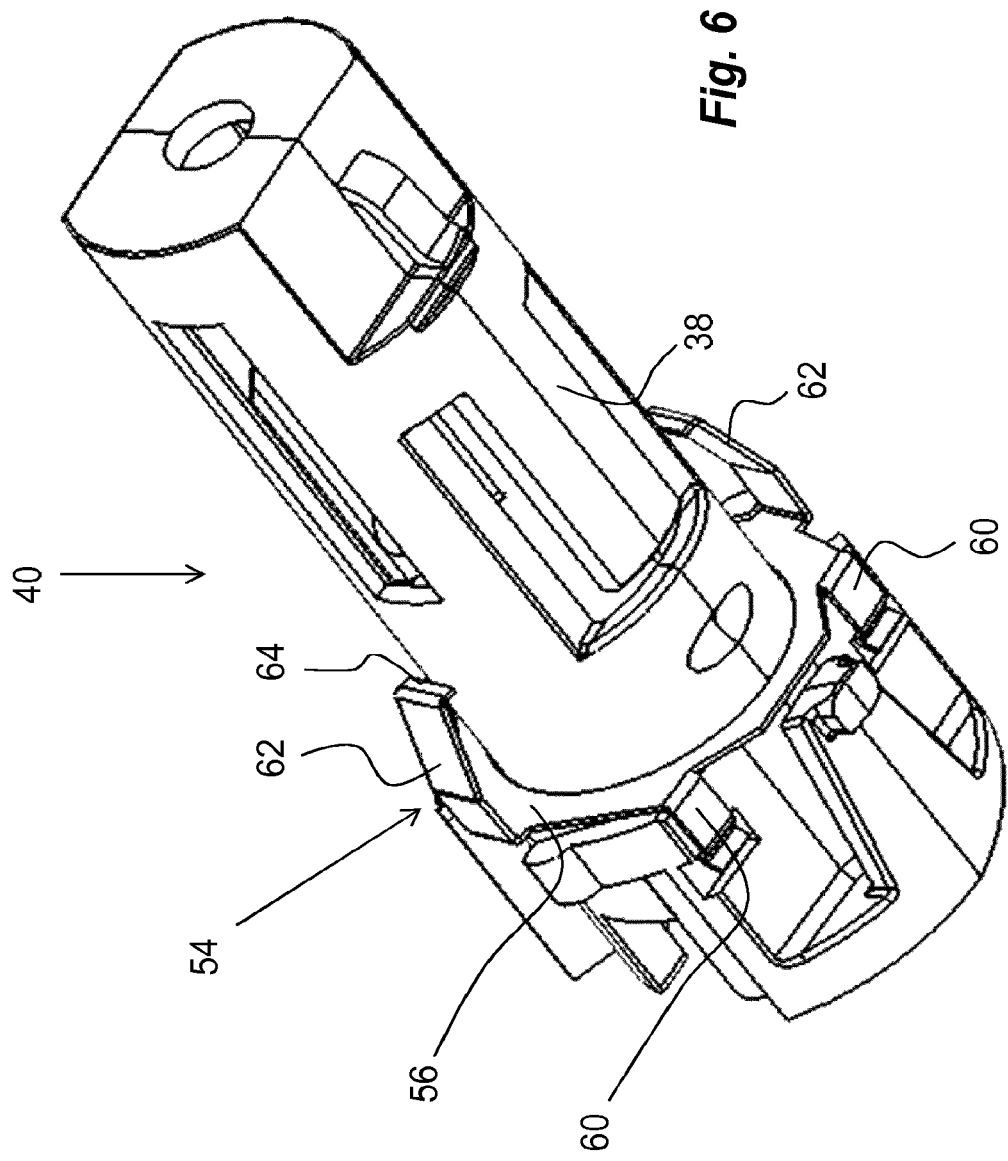
FIG. 6 is another perspective view of the connector shown in FIG. 5.

The connector 40 is further arranged with attachment fixtures 52 for a safety device 54, FIG. 5. The safety device 54 generally comprises a ring-shaped body 56 of a flexible resilient material such as metal. The ring-shaped body has a diameter corresponding to the diameter of the connector 40 and is arranged to abut a circumferential, distally directed surface 58, FIG. 4, on the connector 40. The ring-shaped body 56 is further arranged with attachment tongues 60, which tongues fit into the attachment fixtures 52 for holding the safety device 54 in place. The ring-shaped body further comprises generally distally directed safety elements, in the embodiment shown arranged as tongues 62, FIGS. 6 and 7, preferably with a slight inward inclination and where the free ends of the tongues are provided with inwardly directed ledges 64.

Figure 7:
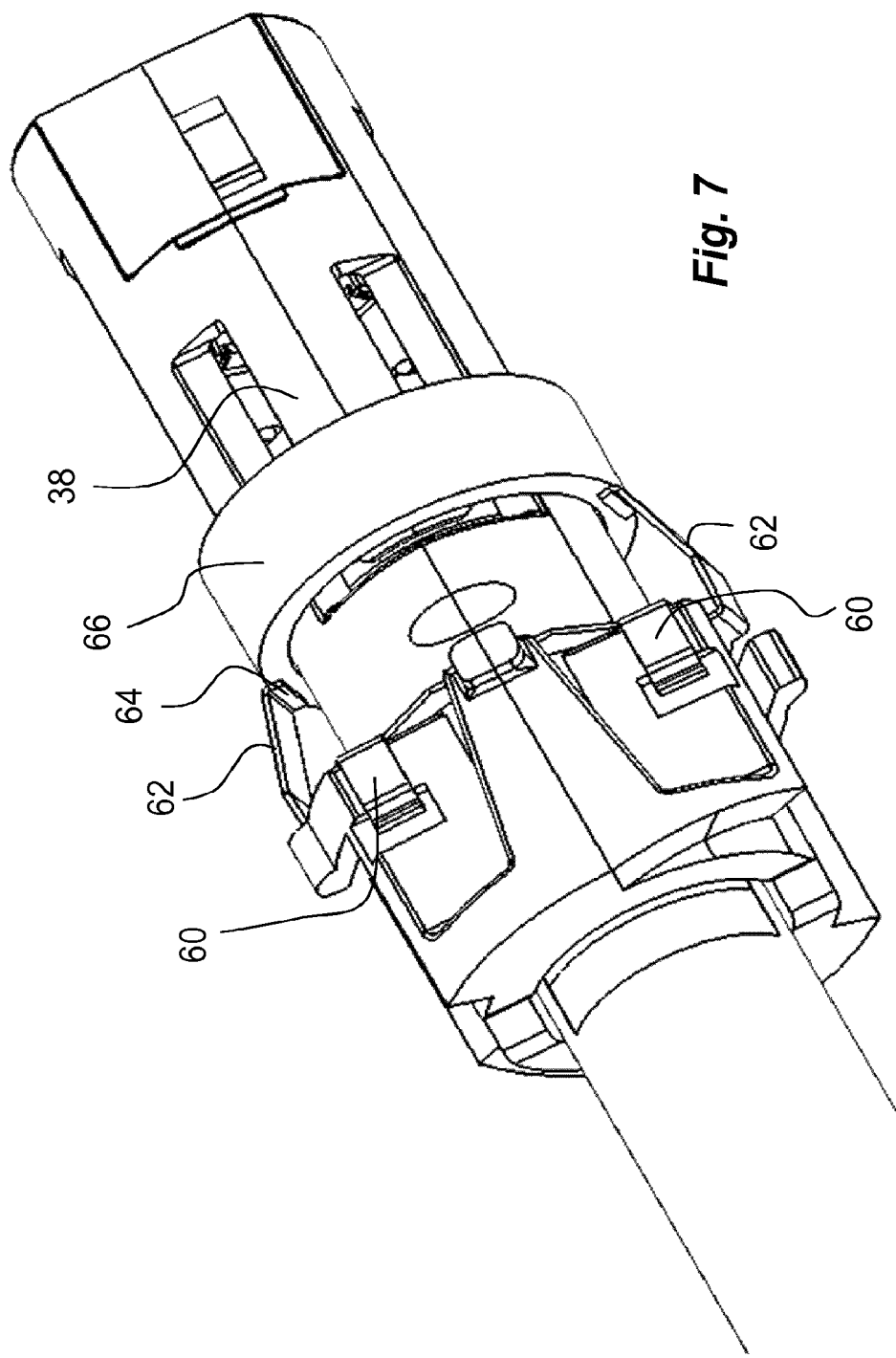
FIG. 7 is a perspective view of the connector and actuator element of the embodiment of FIG. 1.

The distally directed safety elements 62 of the safety device 54 are intended to be in contact with an actuator element 66, FIG. 7. The actuator element 66 is arranged as a ring-shaped member having a diameter generally corresponding to the outer diameter of the connector 40 and initially positioned such that the actuator element 66 is radially outside the holding elements 38, FIG. 7, such that radially outward movement of the holding elements is prevented, as will be described in detail below.

Figure 8:
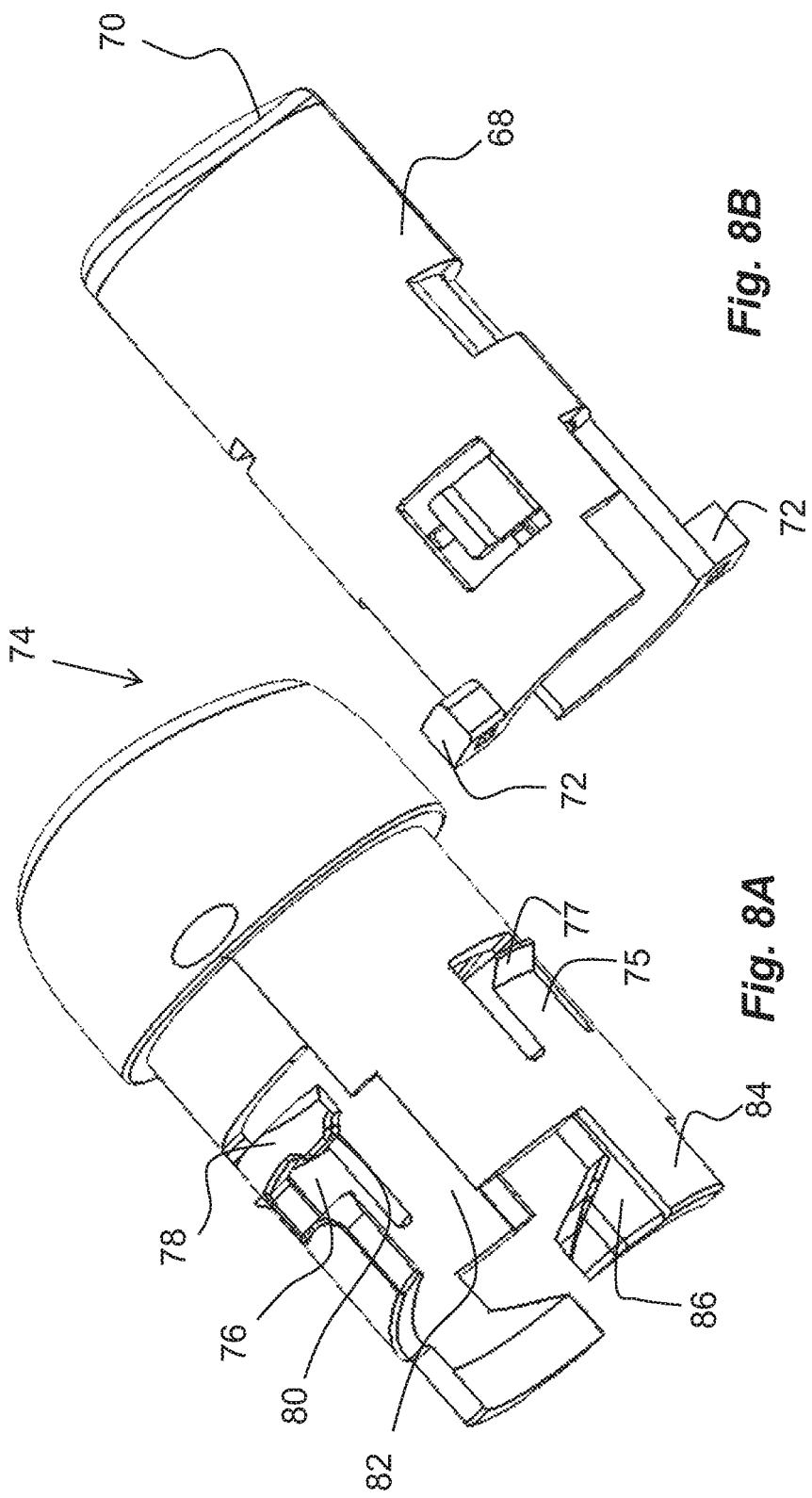
FIG. 8A is a perspective view of the activator of the embodiment of FIG. 1.
FIG. 8B is a perspective view of the actuator of the embodiment of FIG. 1.
Figure 9:
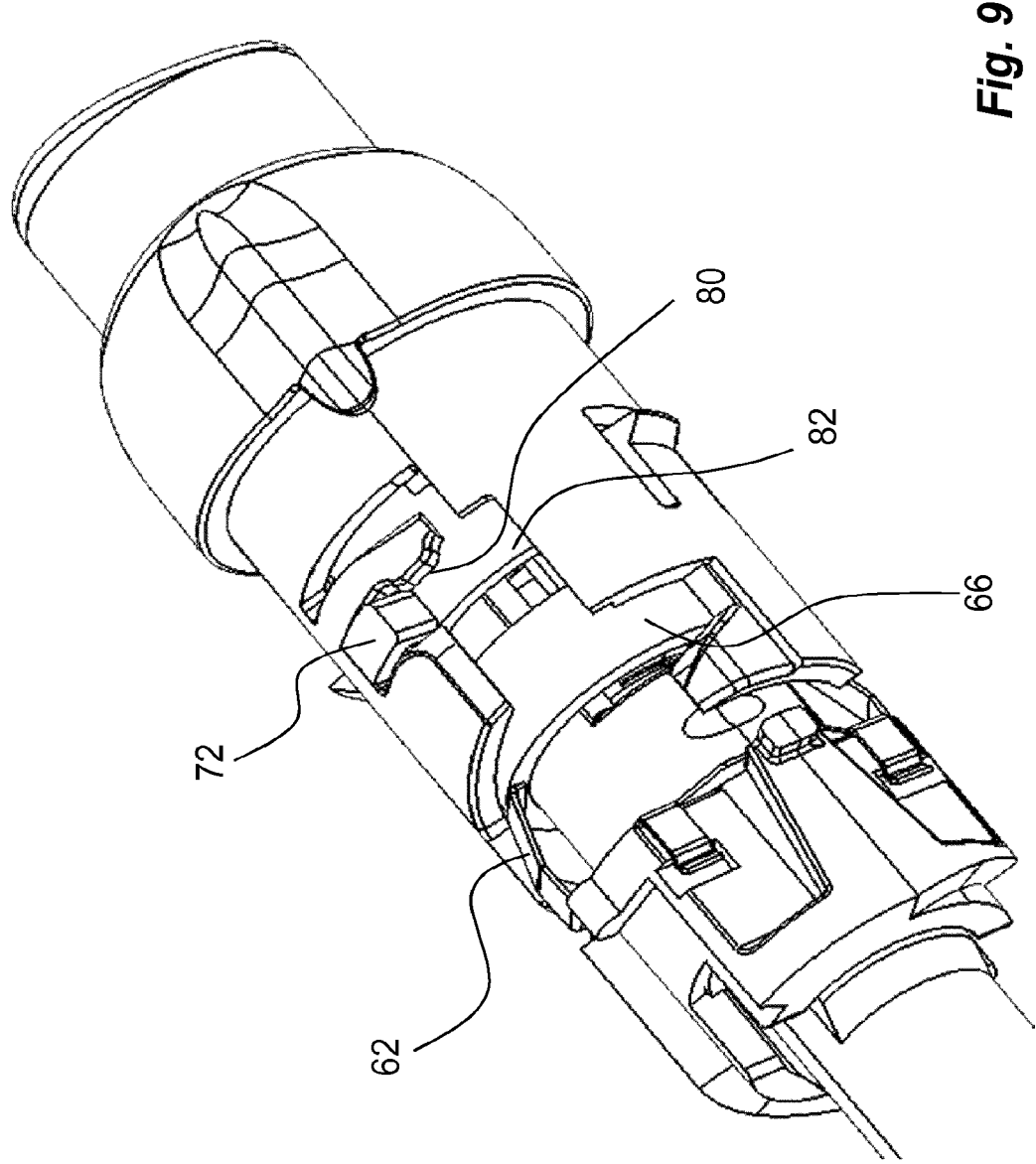
FIG. 9 is a perspective view of a first functional state of the device of FIG. 1.

The device further comprises an actuator 68 shaped as a generally tubular body, FIG. 8B. The tubular body is arranged with a distally directed end surface 70, which will function as a contact surface for a finger of a user. The actuator 68 is further arranged with at least one protrusion 72 at a proximal end and extending outwardly in the radial direction. The protrusions 72 are arranged to come in contact with and act on the actuator element 66 as will be described. The actuator 68 is arranged movable inside a generally tubular activator 74, FIG. 8A, which activator 74 is arranged to be connected to a distal end of the distal housing part. The activator 74 is arranged with cut-outs forming distally directed tongues 75, where the free end of the tongues are arranged with outwardly extending ledges 77. These ledges 77 cooperate with circumferentially extending ledges (not shown) on an inner surface of the distal housing part 12 such that when the activation member is assembled with the distal end of the distal housing part 12, the tongues 75 with the ledges 77 will snap behind the circumferential ledges and lock the activator 74 in the longitudinal direction while allowing turning of the activator 74 in relation to the distal housing part 12 as will be described. The body of the activator 74 is further arranged with at least one generally circumferential groove 76. In the groove 76 a flexible holding arm 78 is arranged in the circumferential direction, FIG. 8B. The free end of the holding arm 78 is arranged with a protrusion 80. The circumferential groove is connected to a generally longitudinally directed groove 82. Further, the proximal end of the activator 74 is arranged with at least one release element, in the embodiment shown a proximally directed arm 84. At the end of the arm a circumferentially directed protrusion 86 is arranged, comprised in the release element, preferably arranged with a wedge-shape, forming a sharp thin edge of the free end of the protrusion 86.

The invention is intended to function as follows. When the device is delivered to a user, the proximal housing part 12 is in an extended position in relation to the distal housing part 14, i.e. the proximal housing part has not been screwed into the distal housing part, as seen in FIG. 3.

Figure 10:
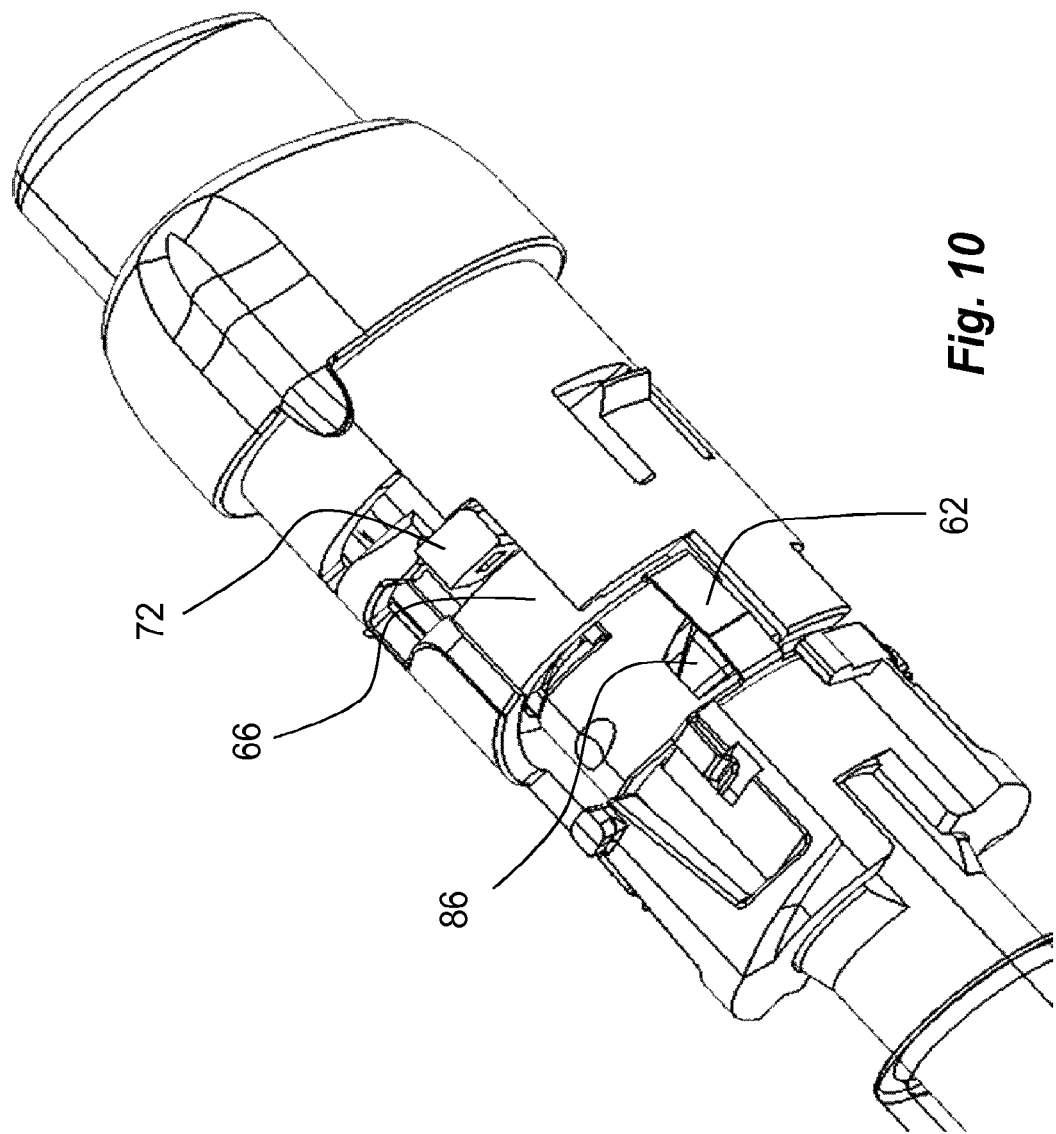
FIG. 10 is a perspective view of a second functional state of the device of FIG. 1.

The activator 74 is in a rotational position such that the protrusions 72 of the actuator 68 are positioned in the circumferential groove 76 of the activator 74 and the flexible holding arm 78 with its protrusion 80 exerts a holding force on the protrusion 72, FIG. 10. Thus the actuator 68 is locked from being depressed because the activator is longitudinally fixed. Further, the ring-shaped actuator element 66 is held in position by the distally directed safety elements 62 of the safety device 54. This ensures that the actuator element 66 cannot be displaced, for example if the device is accidentally dropped on a hard surface. Without the safety device 54, the actuator element 66 could be moved away from its position, whereby the holding members 38 of the connection elements could move out of contact with the plunger rod, whereby the device could be activated unintentionally.

When the device is to be used, the first operation is to attach a medicament delivery member 24. For example an injection needle is attached to the neck portion 22 of the proximal housing part 14. Then the user has to mix the medicament agent with the diluent agent i.e. a mixing step or sequence. The user then engages the two housing parts 12 and 14 and screw-connects them with each other. This causes the proximal housing part 14 to be axially moved inside the distal housing part 12 due to the connection by the threads 16, i.e. the proximal and distal housing parts are moved towards each other from the extended position to the retracted position in order to urge the spring-loaded plunger rod 28 into the medicament container 18, thereby achieving the reconstituted medicament in a manner known in the art.

When the mixing step has been completed, the medicament has been reconstituted and the device is prepared to be activated. This is done by turning the activator 74 in relation to the distal housing part 12. This turning will perform two functions. One function is that the protrusions 72 of the actuator 68 become aligned with the longitudinally directed groove 82 through the relative movement of the activator 74 with regard to the actuator 68, from the locked position past the protrusion 80 of the holding arm 78 and into the longitudinally directed groove 82, FIG. 11, thereby enabling movement in the proximal direction of the actuator 68. The second function is that the release elements, i.e. the wedge-shaped protrusions 86 of the activator 74 are moved in contact with and radially inside the safety elements 62 of the safety device 54. Due to the wedge-shape of the protrusions 86, the safety elements 62 are forced radially outwards, whereby the free ends of the safety elements 62 are moved out of contact with the actuator element 66, whereby the latter is free to be moved.

Now delivery of the reconstituted medicament may be performed. The proximal end of the device, with the medicament delivery member 24, is positioned at the dose delivery site, which could be an injection site if an injection needle is used, at which site a penetration is performed manually. The user then operates the actuator 68 by pressing it axially towards the proximal direction. This in turn causes the actuator element 66 to be proximally moved due to the contact between the actuator 68 and the actuator element 66. The proximal movement of the actuator element 66 causes it to slide along the holding elements 38, FIG. 7. The holding elements 38 are now free to move in the outwardly radial direction, which causes the hooks 42 to move out of contact with its resilient engagement with the recesses 36 of the spring-loaded plunger rod 28. This in turn releases the spring-loaded plunger rod 28 to move in the proximal direction due to the force of the compressed force element 32. The movement of the spring-loaded plunger rod 28 forces the stoppers to move proximally inside the medicament container 18 and thereby expel the reconstituted medicament through the medicament delivery member 24. When the stoppers have reached their end position, i.e. the proximal end position, inside the medicament container 18, the medicament delivery operation is completed.

It is to be understood that the elements and mechanisms described above and shown in the drawings are only examples of structures that may be replaced by other elements and/or mechanisms displaying the same or similar function for obtaining the desired end result. It is further to be understood that the embodiment described above and shown in the drawings is to be regarded only as a non-limiting example of the invention and that it may be modified in many ways within the scope of the patent claims.

The invention claimed is:

1. A medicament delivery device, comprising:
    a proximal housing arranged to accommodate a medicament container;
    a distal housing comprising a drive unit, where the drive unit comprises:
        a plunger rod;
        a connector arranged to releasably hold the plunger rod;
        an actuator element slidably arranged around the connector such that the actuator element axially moves proximally relative to the connector from a locking position to an unlocking position, where in the locking position the actuator element prevents disengagement of the connector from the plunger rod and in the unlocking position the actuator element allows disengagement of the connector from the plunger rod;
        a safety device fixedly attached to the connector and abutting the actuator element when the actuator element is in the locking position, where the safety device prevents the actuator element from moving proximally from the locking position to the unlocking position;
        an actuator slidably arranged within an activator, where the activator is rotatably engaged with the distal housing and having a first position and a second position, where in the first position the actuator and the activator are in a locked engagement such that the actuator is prevented from moving proximally relative to the activator,
    wherein the fixed attachment of the safety device with the connector prevents rotational and axial movement of the safety device relative to the connector,
    wherein rotation of the activator from the first position to the second position unlocks the actuator so that the actuator can move proximally to engage and move the actuator element proximally.

2. The medicament delivery device of claim 1 wherein rotation of the activator from the first position to the second position moves the safety device from abutting the actuator element to allow the actuator element to move to the unlocking position.

3. The medicament delivery device of claim 1 wherein an axial force in a proximal direction applied to the activator when in the first position will not cause the actuator to engage and move the actuator element in the proximal direction relative to the connector.

4. The medicament delivery device of claim 1 wherein an axial force in a proximal direction applied to the activator when in the second position causes the actuator to engage and move the actuator element in the proximal direction relative to the connector such that the connector disengages from the plunger rod.

5. The medicament delivery device of claim 1 wherein the actuator further comprises a protrusion that slidably engages a circumferential groove of the activator when the activator is in the first position.

6. The medicament delivery device of claim 5 wherein the protrusion slidably moves out of the groove as the activator moves from the first position to the second position and becomes aligned with a longitudinal groove in the activator.

7. The medicament delivery device of claim 1 where the plunger rod is hollow and encloses a tensioned force member exerting a biasing force on the plunger rod in a proximal direction.

8. The medicament delivery device of claim 1 wherein the connector further comprises radially movable holding elements that releasably prevent axial movement of the plunger rod.

9. The medicament delivery device of claim 8 where proximal axial movement of the actuator element from the locking position to the unlocking position causes the holding elements to flex radially outward releasing the plunger rod so it can move proximally.

10. The medicament delivery device of claim 1, wherein at least a portion of the safety device is metal.

11. The medicament delivery device of claim 1 where the safety device in the locking position has a distal facing end that abuts a proximal facing end of the actuator element to prevent axial movement of the actuator element relative to the connector and in the unlocking position the distal facing end no longer abuts the proximal facing end of the actuator element allowing the actuator element to axially move in the proximal direction.

12. The medicament delivery device of claim 1 where the medicament container comprises two chambers separated by a movable first stopper and sealed by a movable second stopper, where connection of the proximal housing to the distal housing causes the second stopper to move proximally to abut the first stopper.

13. The medicament delivery device of claim 1 where the actuator element is ring-shaped and is slidably positioned around the connector in both the locking position and the unlocking position.

14. A medicament delivery device, comprising:
    a proximal housing arranged to accommodate a medicament container;
    a distal housing comprising a drive unit, where the drive unit comprises:
        a plunger rod;
        a connector arranged to releasably hold the plunger rod;
        an actuator element slidably arranged around the connector such that the actuator element axially moves proximally relative to the connector from a locking position to an unlocking position, where in the locking position the actuator element prevents disengagement of the connector from the plunger rod and in the unlocking position the actuator element allows disengagement of the connector from the plunger rod;

a safety device fixedly attached to the connector and abutting the actuator element when the actuator element is in the locking position, where the safety device prevents the actuator element from moving proximally from the locking position to the unlocking position;

an actuator comprising a protrusion and slidably arranged within an activator comprising a circumferential groove, where the activator is rotatably engaged with the distal housing and having a first position and a second position, where in the first position the actuator and the activator are in a locked engagement such that the actuator is prevented from moving proximally relative to the activator, wherein rotation of the activator from the first position to the second position unlocks the actuator so that the actuator can move proximally to engage and move the actuator element proximally.

15. The medicament delivery device of claim 14 where the protrusion slidably engages a circumferential groove of the activator when the activator is in the first position preventing axial movement of the actuator in the proximal direction.

16. The medicament delivery device of claim 15 wherein the protrusion slidably moves out of the groove as the activator moves from the first position to the second position and becomes aligned with a longitudinal groove in the activator.

17. The medicament delivery device of claim 14 where the plunger rod is hollow and encloses a tensioned force member exerting a biasing force on the plunger rod in a proximal direction.

18. The medicament delivery device of claim 14 where the actuator further comprises a tubular body positioned within the activator and having a distally directed end surface protruding through an open distal end of the activator providing a contact surface for manual manipulation by a user of the medicament delivery device.

19. The medicament delivery device of claim 14 where the activator further comprises a circumferentially directed protrusion that engages the safety device when the activator is rotated causing the safety device to no longer abut the actuator element.

20. A medicament delivery device, comprising:

a proximal housing arranged to accommodate a medicament container;

a distal housing comprising a drive unit, where the drive unit comprises:

a plunger rod;

a connector arranged to releasably hold the plunger rod;

an actuator element slidably arranged around the connector such that the actuator element axially moves proximally relative to the connector from a locking position to an unlocking position, where in the locking position the actuator element prevents disengagement of the connector from the plunger rod and in the unlocking position the actuator element allows disengagement of the connector from the plunger rod;

a safety device fixedly attached to the connector and located proximal of the actuator element when the actuator element is in the locking position such that the actuator element is prevented from moving proximally from the locking position to the unlocking position;

an actuator slidably arranged within an activator, where the activator is rotatably engaged with the distal housing and having a first position and a second position, where in the first position the actuator and the activator are in a locked engagement such that the actuator is prevented from moving proximally relative to the activator, wherein the fixed attachment of the safety device with the connector prevents rotational and axial movement of the safety device relative to the connector, wherein rotation of the activator from the first position to the second position unlocks the actuator so that the actuator can move proximally to engage and move the actuator element proximally.

* * * * *